United States Patent [19]

Gehrken et al.

[11] Patent Number: 4,645,845
[45] Date of Patent: Feb. 24, 1987

[54] NOVEL OPTICALLY ACTIVE CHROMAN DERIVATIVES, THEIR PREPARATION AND NOVEL INTERMEDIATES

[75] Inventors: Henning-Peter Gehrken, Lambsheim; Hansgeorg Ernst, Ludwigshafen; Joachim Paust, Neuhofen, all of Fed. Rep. of Germany

[73] Assignee: BASF Aktiengesellschaft, Ludwigshafen, Fed. Rep. of Germany

[21] Appl. No.: 588,365

[22] Filed: Mar. 12, 1984

[30] Foreign Application Priority Data

Mar. 15, 1983 [DE] Fed. Rep. of Germany ....... 3309159

[51] Int. Cl.$^4$ ........................................... C07D 311/72
[52] U.S. Cl. ..................................... 549/407; 549/408
[58] Field of Search ............................... 549/407, 408

[56] References Cited

U.S. PATENT DOCUMENTS 4,003,919 1/1977 Scott et al. ........................... 549/407

OTHER PUBLICATIONS

Cohen et al, J. Org. Chem., 41, (1976), p. 3505.
Scott et al., Helvetica Chimica Acta, 59, (1976), p. 290.

Primary Examiner—Nicky Chan
Attorney, Agent, or Firm—Oblon, Fisher, Spivak, McClelland & Maier

[57] ABSTRACT

Novel optically active chroman derivatives of the general formulae Ia and Ib

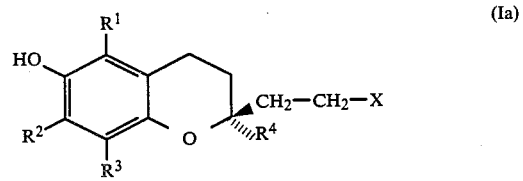

(Ia)

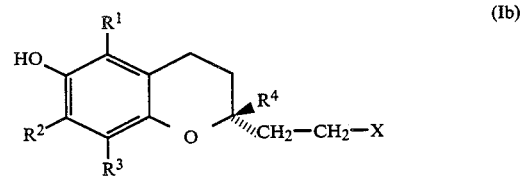

(Ib)

where $R^1$, $R^2$, $R^3$ and $R^4$ are each hydrogen or alkyl and X is —OH, —O—CO-alkyl, —O-alkyl, —O-tosyl, —O-mesyl, —O-benzenesulfonyl, Cl, Br or I, are prepared by a process in which (a) the racemate of the formula I'

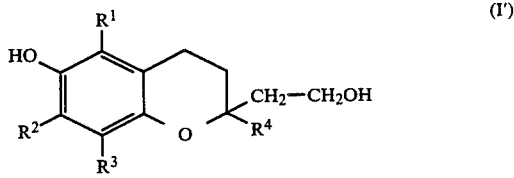

(I')

is esterified in the side chain with a carboxylic acid and then acylated with an optically active carboxylic acid halide of the general formula III

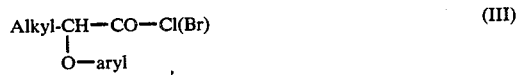

(III)

or with the corresponding carboxylic anhydride, to give a chroman derivative IV

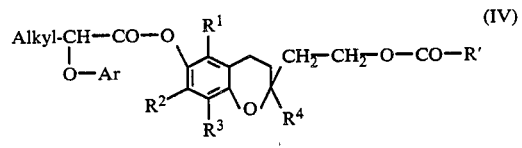

(IV)

or (b) the racemate I' is esterified in the side chain with the carboxylic acid from which III is derived, and, if required, the resulting ester is acylated with a carboxylic acid halide to give IV'

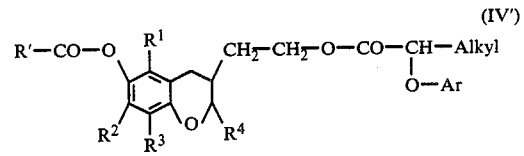

(IV')

the resulting mixture IV or IV', which consists of two diastereomers, is resolved by fractional crystallization, the diastereomers are hydrolyzed to the alcohols Ia and Ib and, if desired, these are converted to the other compounds Ia and Ib in a conventional manner.

Useful optically active chroman derivatives Ia and Ib and diastereomeric chromanyl esters IV and IV' are also claimed.

6 Claims, No Drawings

NOVEL OPTICALLY ACTIVE CHROMAN DERIVATIVES, THEIR PREPARATION AND NOVEL INTERMEDIATES

The present invention relates to a process for the preparation of novel optically active chroman derivatives of the general formulae Ia and Ib

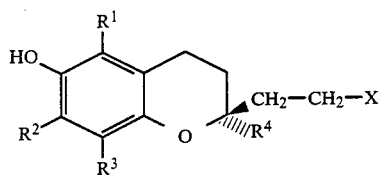

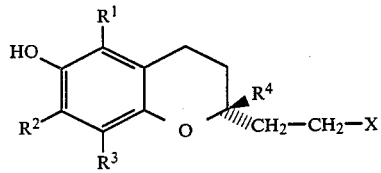

where $R^1$, $R^2$, $R^3$ and $R^4$ are each hydrogen or $C_1$-$C_4$—alkyl and X is —OH, —O—CO—$R^6$, —O—$R^6$, —O—tosyl, —O—mesyl, —O—benzenesulfonyl, Cl, Br or I, where $R^6$ is $C_1$-$C_4$—alkyl.

The present invention furthermore relates to the particularly useful members of this novel group of compounds, ie. the optically active chroman derivatives of the formulae Ia and Ib, where $R^1$, $R^2$, $R^3$ and $R^4$ are each methyl and X is —OH, Cl, Br, I, —O—CH$_3$, —O—tert.-butyl, —O—CO—CH$_3$ or —O—tosyl, in particular Br, Cl or O-tosyl.

The present invention furthermore relates to diastereomeric esters of the general formulae IV and IV'

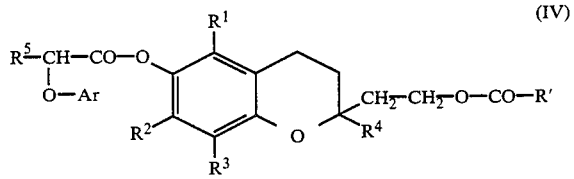

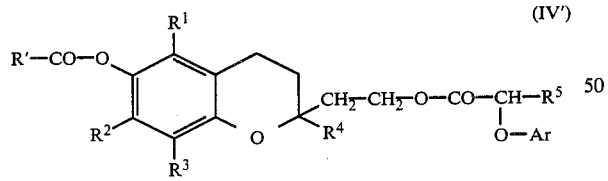

where $R^5$ is a $C_1$-$C_3$—alkyl, R' is $C_1$-$C_4$—alkyl and Ar is aryl which in turn can be substituted, these esters being novel intermediates in the preparation process.

Particular examples of chroman derivatives of the formulae Ia and Ib are
(S)-2,5,7,8-tetramethyl-6-hydroxy-2-(2-hydroxyethyl)-chroman, (R)-2,5,7,8-tetramethyl-6-hydroxy-2-(2-hydroxyethyl)-chroman, (S)-2,5,7,8-tetramethyl-6-hydroxy-2-(2-bromoethyl)-chroman (R)-2,5,7,8-tetramethyl-6-hydroxy-2-(2-bromoethyl)-chroman, (S)-2,5,7,8-tetramethyl-6-hydroxy-2-(2-chloroethyl)-chroman and (R)-2,5,7,8-tetramethyl-6-hydroxy-2-(2-chloroethyl)-chroman, among which the (S) derivatives having a leaving group in the side chains are particularly important for the preparation of (2R, 4'R, 8'R)- and (2R, 4'RS, 8'RS)-tocopherol.

Examples of diastereomeric esters of the formulae IV and IV' are
2,5,7,8-tetramethyl-6-[2'-(o-methyl-p-chlorophenoxy)-propionyl]-2-(2-acetoxyethyl)-chroman;
2,5,7,8-tetramethyl-6-acetoxy-2-[2-($\alpha$-naphth-2'-yloxy)-propionylethyl]-chroman and
2,5,7,8-tetramethyl-6-hydroxy-2-[2-($\alpha$-naphth-2'-yloxy)-propionylethyl]-chroman.

The substituents in the optically active compounds of the formulae Ia and Ib and of the other structural formulae used in this application are denoted by the symbol ▲ where they lie in front of the plane of the molecule, and by the symbol   where they lie behind the plane of the molecule. In the case of structural formulae where the stereochemistry of the substituents is not specially indicated, the substituents can have either an R or an S orientation, or the substance may be a mixture of the R and S isomers.

The chroman derivatives of the formulae Ia and Ib, where $R^1$, $R^2$, $R^3$ and $R^4$ are each methyl and X is a leaving group, are very important for the preparation of $\alpha$-tocopherol (vitamin E); depending on whether they are in the 2R-, 2S- or 2RS form, they are key substances for the preparation of both natural optically active $\alpha$-tocopherol (2R, 4'R, 8'R-$\alpha$-tocopherol) and other optically active isomers, in particular (2R, 4'RS, 8'RS)-$\alpha$-tocopherol, which is likewise very biologically active.

German Laid-Open Application DOS No. 2,602,509 discloses that tocopherol can be synthesized by coupling a chroman derivative of the formula

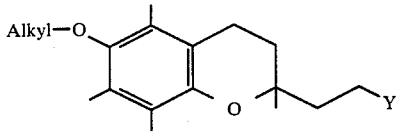

where Y is a leaving group, with a suitable $C_{14}$ Grignard compound, by the Schlosser-Fouquet method. An optically active chroman building block suitable for this synthesis can be prepared by one of the methods described in German Laid-Open Application DOS No. 2,364,165.

In this process, the chroman derivative of the formula

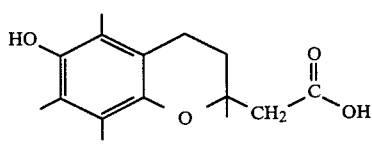

is resolved into the optical antipodes via a diastereomeric salt pair, with the aid of an optically active base, eg. phenylethylamine. The resulting optically active chromanylacetic acid, after esterification and protection of the phenolic hydroxyl group, can then be reduced to the corresponding optically active chromanylethanol, which can be tosylated to give a chroman derivative which is capable of coupling by the method described in German Laid-Open Application DOS No. 2,602,509. When the data due to Cohen et al. in J. Org. Chem. 41 (1976), 3505 and Scott et al. In Helv. Chim. Acta 59 (1976), 290 et seq. are also taken into account, the following overall reaction route emerges for the preparation of such a chroman derivative capable of coupling:

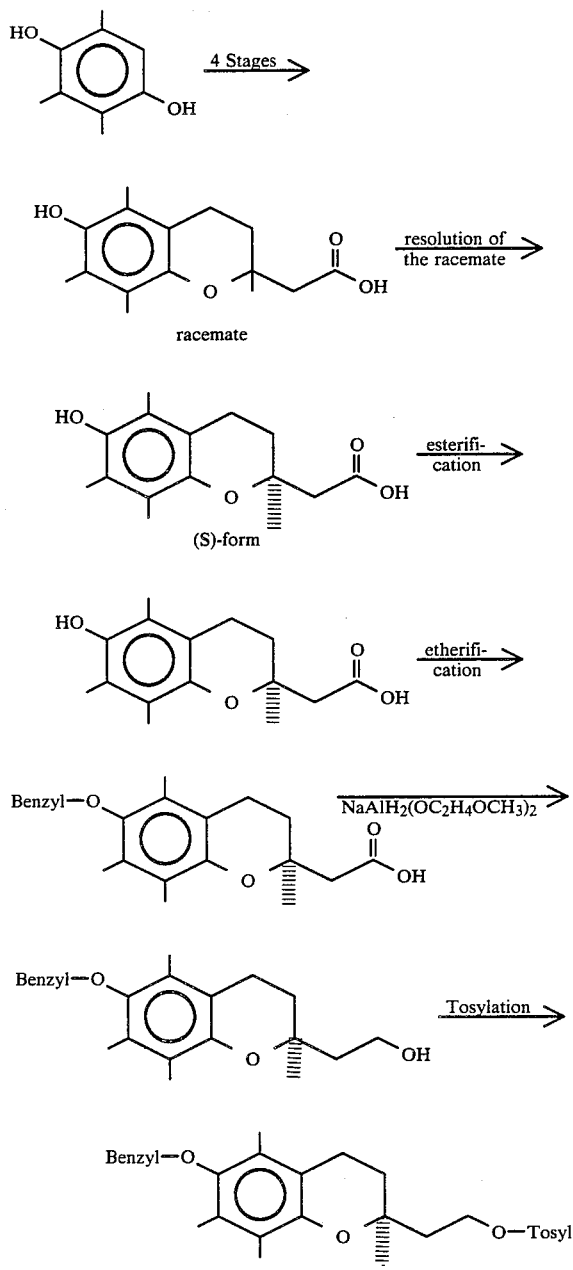

This process is very involved and, moreover, requires the use of expensive hydrides, eg. NaAlH$_2$(OC$_2$H$_4$OCH$_3$)$_2$, in the hydrogenation stage.

It is therefore an object of the present invention to provide, in a simpler and cheaper manner, chroman derivatives which are capable of coupling to give (2R, 4'R, 8'R)— or (2R, 4'RS, 8' (RS)-α-tocopherol.)

We have found that this object is achieved, and that the chroman derivatives Ia and Ib defined at the outset are obtained, if (a) the racemate I'

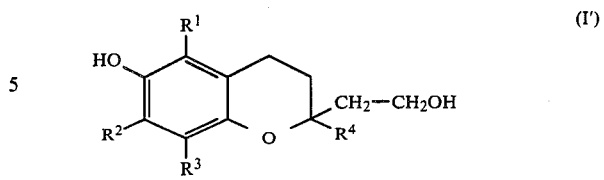

is selectively converted with a carboxylic acid of the formula II $$R'\text{—COOH} \qquad (II)$$

where R' is C$_1$-C$_4$—alkyl, or with a lower alkyl ester of such an acid, to the ester I''

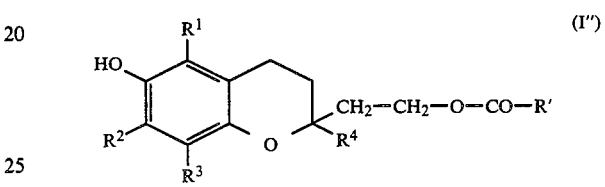

this is acylated with an optically active carboxylic acid halide of the general formula III $$\begin{array}{c} R^5\text{—CH—CO—Y} \\ | \\ O\text{—Ar} \end{array} \qquad (III)$$

where R$^5$ is C$_1$-C$_3$—alkyl, Y is Cl or Br and Ar is aryl which in turn can be substituted, or with the corresponding carboxylic anhydride of the general formula V $$\begin{array}{c} R^5\text{—CH—CO—O—CO—CH—R}^5 \\ | \qquad\qquad\qquad\qquad | \\ O\text{—Ar} \qquad\qquad\qquad O\text{—Ar} \end{array} \qquad (V)$$

to give the chroman derivative IV

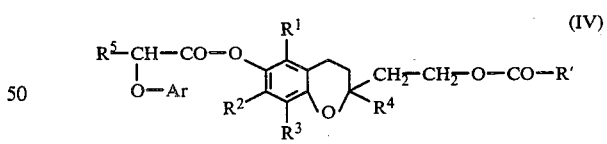

which consists of two diastereomeric esters, this is resolved by fractional crystallization, pure diastereomers are hydrolyzed in a conventional manner to give the alcohols of the formulae Ia and Ib, and, if desired, these are converted in a conventional manner to the other compounds of the formulae Ia and Ib, or if (b) the racemate I' is converted with a carboxylic acid III'

$$\begin{array}{c} R^5\text{—CH—COOH} \\ | \\ O\text{—Ar} \end{array} \qquad (III')$$

or with a lower alkyl ester of this, to an ester I'''

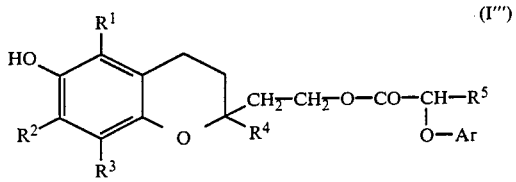

this is, if desired, acylated with a carboxylic acid halide of the formula R'—CO—X$^1$, where X$^1$ is Cl, Br or I, or with the corresponding carboxylic anhydride, to give IV'

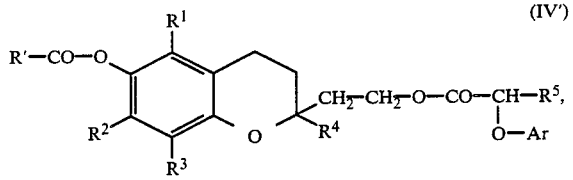

I''' or IV', which consists of two diastereomers, is resolved by fractional crystallization, the pure diastereomers are hydrolyzed in a conventional manner to give the alcohols of the formulae Ia and Ib, and, if desired, these are converted in a conventional manner to the other compounds of the formulae Ia and Ib.

In both embodiments of the novel process, the starting material is the racemic chroman derivative I', which is disclosed in German Laid-Open Application DOS No. 3,010,505, and is readily obtainable by means of a Friedel-Crafts addition reaction of 1-vinylpropane-1,3-diol

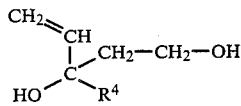

with the hydroquinone

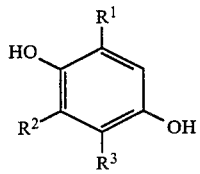

I' has two functional hydroxyl groups, ie. one alcoholic and one phenolic hydroxyl group, which, because of their different reactivities, can be readily esterified selectively, in accordance with general laws.

The esterification of the alcoholic hydroxyl group is carried out using a free acid or a lower alkyl ester as a mild esterification agent, whereas the subsequent esterification of the phenolic hydroxyl group requires the use of the corresponding acid halide as a stronger esterification agent.

In the novel process, the acid radical of the optically active acid III' conforming to the definition can be bonded to either the alcoholic or phenolic hydroxyl group of I', as in the embodiments (a) and (b). In both cases, diastereomeric biesters are obtained, ie. IV and IV'; contrary to expectation, these can be readily resolved into their diastereomers by fractional crystallization.

The introduction of the radical of the optically active acid III' is common to both embodiments of the process, whereas the esterification with the inactive acid II is required only in embodiment (a) and can be dispensed with in embodiment (b).

A particularly suitable inactive lower carboxylic acid II is acetic acid, but propionic acid, butyric acid and isobutyric acid may also be used.

Particularly suitable acids III' (these correspond to the acid radicals of III) are those in which R$^5$ is methyl. The aryl group Ar is phenyl in the simplest case, but the α- and β-naphthyl groups and substituted phenyl and naphthyl groups are also suitable. Examples of substituents on Ar are C$_1$-C$_4$—alkyl, C$_1$-C$_4$—alkoxy, chlorine or bromine, cyano and nitro. Preferably, the phenyl or naphthyl groups should carry no more than two of these substituents.

The optically active acids III' are known, or are obtainable by a conventional method. To our knowledge, they have not to date been employed for the resolution of racemates. The acid derivatives III are obtainable from the free acids in a conventional manner, eg. by reaction with, for example, thionyl chloride. Other suitable optically active reagents are the corresponding anhydrides of the formula V.

Particularly preferred acids III' or acid halides III are the optically active forms of 1-phenoxypropionic acid, of 2-(2'-methyl-4'-chlorophenoxy)-propionic acid and of 1-(naphth-1-yloxy)-propionic acid.

Regarding the two embodiments of the process, the following may be stated specifically: In embodiment (a), the esterification of I' with the C$_2$-C$_4$-fatty acid II is carried out, as usual, preferably in an organic solvent. Examples of suitable solvents are benzene, toluene, ethyl acetate and mixtures of these.

Examples of suitable esterification catalysts are sulfuric acid and p-toluenesulfonic acid.

The same conditions also apply when the free acid is replaced with its lower alkyl ester, the methyl ester preferably being used in this case. The transesterification has the advantage that no aqueous phase is formed when the reaction is carried out in a water-insoluble solvent.

The resulting esters I'' can be isolated, but it is also possible to carry out the acylation with III directly if significant amounts of water or alcohols are not present.

The acylation of the phenolic hydroxyl group with the acid chloride III is carried out, as usual, preferably in the presence of an equimolar amount of a tertiary nitrogen base, such as pyridine, as an acid acceptor. When the acylation is complete, water is added to the reaction mixture in the usual manner, the organic phase is separated off by a conventional procedure, and, if required, the solvent is removed from this.

The residue, which consists of the diastereomers IV, is taken up in a solvent, and the solution is fractionally crystallized in a conventional manner.

Suitable solvents are those mentioned in connection with the esterification reaction, as well as C$_1$-C$_4$—alkanols, in particular methanol and ethanol.

Using a conventional technique, IV which crystallizes out when the extracts are evaporated down is first dissolved completely in a hot solvent, and one of the diastereomers is then obtained by crystallization when the resulting solution cools. If necessary, the crystallization should be repeated once or twice, depending on the desired purity.

The diastereomers which have been separated are finally hydrolyzed in a conventional manner, preferably using aqueous alcoholic potassium hydroxide solution. The alcohol of the formula Ia or Ib is then extracted in a conventional manner with a solvent, eg. methylene chloride, which is not miscible with the aqueous alcoholic phase.

The alcohols of the formulae Ia and Ib are obtained by method (a), ie. via esterification, recrystallization and hydrolysis, as a rule in yields of from 25 to 30%, based on the racemate I', ie. in yields of from 50 to 60% of theory.

Method (b) is a similar preparative procedure to method (a), with the difference that in this case the alcoholic hydroxyl groups of I' is first esterified with the free optically active acid III' or with a lower alkyl ester of this. The acylation of the phenolic hydroxyl group with the acid halide II' is in principle unnecessary, but is advantageous because the bisesters frequently crystallize more readily than the monoesters.

Furthermore, the novel process for the resolution of racemates has a decisive though unexpected advantage due to the special solubility relationships between monoesters and bisesters. If the racemate I' is first esterified, for example with (−)-1-(naphth-1-yloxy)-propionic acid, the reaction mixture is worked up in a conventional manner by shaking with water and extracting, the combined extracts are evaporated down, the resulting crude ester is dissolved in methanol or ethanol, and the solution is seeded, (R)-2,5,7,8-tetramethyl-6-hydroxychroman-2-yl-ethyl (−)-1-(naphth-1-yloxy)-propionate slowly crystallizes out. This can be converted to (R)-2,5,7,8-tetramethyl-6-hydroxy-2-(2-hydroxyethyl)-chroman by hydrolysis (cf. Example 5). If the mother liquor which has been separated off is then evaporated down, the diastereomer mixture which then has a high concentration of the (S)-2,5,7,8-tetramethyl-6-hydroxy-2-(2-hydroxyethyl)-chroman ester is acetylated in the 6-position, for example with acetyl chloride or acetic anhydride, the reaction mixture is worked up in a conventional manner and the resulting crude bisester is dissolved in hot methanol or ethanol, surprisingly the bisester of the (S)-chroman derivative crystallizes out first. This can be converted to (S)-2,5,7,8-tetramethyl-6-hydroxy-2-(2-hydroxyethyl)-chroman by hydrolysis.

All of the subsequent steps in the process for the resolution of the racemate are similar to those of embodiment (a). Accordingly, a particularly advantageous embodiment of the novel process is carried out as follows: the racemate I' is converted with a carboxylic acid III', or with a lower alkyl ester of this, to a mixture of diastereomeric esters I''', this mixture is dissolved in an alcohol, the (R) form which first crystallizes out during this procedure is separated off, the monoester which remains in the isolated mother liquor and predominantly consists of the (S) form is esterified in the 6-position with a carboxylic acid halide of the formula R'—CO—X, where X is Cl, Br or I, or with the corresponding carboxylic anhydride, and the (S) form of the chroman derivative IV', which now crystallizes out preferentially, is isolated from the solution of the diastereomers IV' which predominantly contains this form. The pure diastereomers are hydrolyzed in a conventional manner to give the alcohols of the formulae Ia and Ib, and, if desired, these are converted to the other compounds of the formulae Ia and Ib in a conventional manner.

Finally, the following may be stated regarding the novel process for the resolution of racemic 2,5,7,8-tetramethyl-6-hydroxy-2-(2-hydroxyethyl)-chroman into its (R) and (S) form. The optically active acids III' and their derivatives have not been used to date for the resolution of racemates. It is surprising that the novel racemate resolution procedure using these optically active acids or their derivatives can be carried out so advantageously, since attempts to resolve chromanylethyl acetate with the aid of optically active acid derivatives, eg. (−)-menthyloxyacetyl chloride (cf. S. Fujise et al, Chem. Ber. 69 (1936), 1893 and A. E. Knauf et al, Am. Chem. Soc. 56, (1934), 2109), which are known from the literature to be useful for resolving racemic mixtures of phenolic compounds gave unsatisfactory results. Moveover, it is surprising that resolution of the racemate takes place in such an advantageous manner even when the radical of the optically active acid is bonded to the phenolic hydroxyl group of the chroman ring and is therefore very far away from the chiral carbon atom of the chroman derivative. Furthermore, it could not be foreseen that, as a result of the special solubility relationships between the chromanylethyl monoesters and bisesters, it would be possible to isolate both diastereomeric forms of the chroman derivative in a simple manner using only one optically active form of the acid (cf. Examples 3 and 5). This of course means that the more desirable (S)-2,5,7,8-tetramethyl-6-hydroxy-2-(2-hydroxyethyl)-chroman can be obtained using, for example, either (−)-1-(naphth-1-yloxy)-propionic acid (cf. Example 3) or (+)-1-(naphth-1-yloxy)-propionic acid (cf. Example 6).

The chroman derivatives of the formulae Ia and Ib which are initially obtained when the racemate is resolved and in which X is OH are converted in a conventional manner to the other chroman derivatives conforming to the definition, so that detailed information in this context is unnecessary.

For example, (S)- and (R)-2,5,7,8-tetramethyl-6-hydroxy-2-(2-bromoethyl)-chroman are obtained by reacting the corresponding -2-(2-hydroxyethyl)-chroman with a solution of triphenylphosphine and bromine in anhydrous methylene chloride, and (S)- and (R)-2,5,7,8-tetramethyl-6-hydroxy-2-(2-chloroethyl)-chroman are obtained by reacting the corresponding -2-(2-hydroxyethyl)-chroman with $CCl_4$ and triphenylphosphine. Regarding further details of these processes, reference may be made to E. Schacht in "Kontakte", issue 3, page 9, 1974, and literature cited therein.

(S)- and (R)-2,5,7,8-tetramethyl-6-hydroxy-2-(2-tert.-butoxyethyl)-chroman are obtained by reacting a solution of the corresponding -2-(2-hydroxyethyl)-chroman in methylene chloride with isobutene in the presence of a small amount of sulfuric acid by a method similar to that described by H. C. Beyerman et al. in Rec. Trav. Chim. 84 (1965), 203.

The present invention permits the preparation of optically active chroman derivatives, capable of coupling to form α-tocopherol, by a sequence of synthesis stages which, compared with the prior art, is very short and easy to carry out:

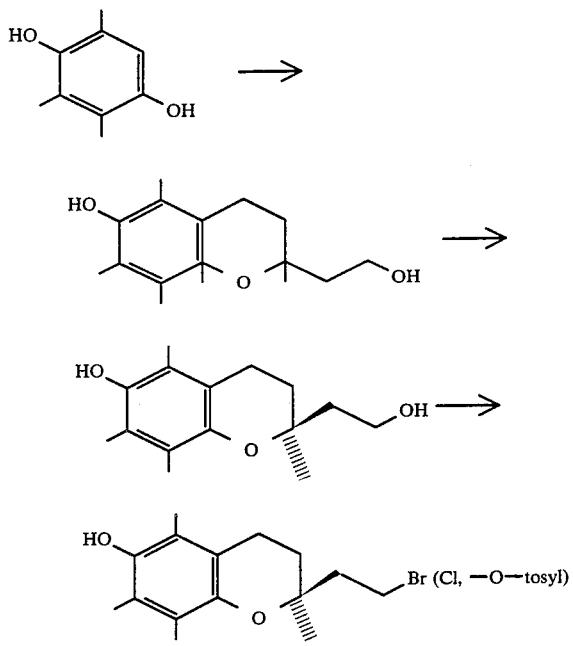

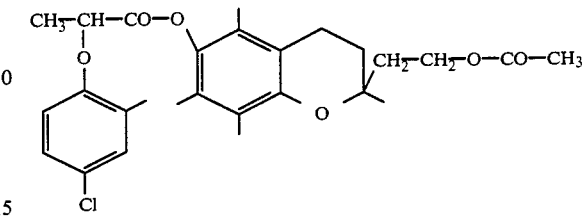

The novel chroman derivatives of the formula Ia, where X is Cl, Br or O—tosyl, can be directly bonded to an appropriate $C_{14}$ Grignard compound under catalysis with a di-(alkali metal) tetrahalocuprate in accordance with the Schlosser-Fouquet method to give an α-tocopherol isomer, the reaction being carried out very advantageously by the process described in a patent application filed on the same date.

EXAMPLE 1

Preparation of (S)-2,5,7,8-tetramethyl-6-hydroxy-2-(2-hydroxyethyl)-chroman by embodiment (a)

(a) 200 g (800 millimoles) of racemic 2,5,7,8-tetramethyl-6-hydroxy-2-(2-hydroxyethyl)-chroman (I') were esterified in a conventional manner with 100 g of glacial acetic acid in the presence of 4 g of p-toluene sulfonic acid and 1.5 liters of ethyl acetate in the course of 6 hours, under reflux.

Working up in a conventional manner gave the acetate of I' (2,5,7,8-tetramethyl-6-hydroxy-2-(2-acetoxyethyl)-chroman) in the form of a yellow oil, which was recrystallized from ethanol. Mp.=74° C., yield=85% of theory.

(b) L-(4-chloro-2-methyl)-phenoxypropionyl chloride, obtained by heating 80 g (374 millimoles) of L-(4-chloro-2-methyl)-phenoxypropionic acid with 125 g of thionyl chloride at 50° C. for 3 hours and distilling off the excess thionyl chloride, was added gradually, at 0° C., to a solution of 100 g of the ester prepared as described in Example 1a, in 250 ml of pyridine.

The reaction mixture was stirred for a further 16 hours at room temperature and then poured into ice water. The resulting aqueous organic mixture was extracted with methylene chloride, and the organic phase obtained was washed with 5N HCl, water and dilute sodium carbonate solution and once again with water, and was then dried and evaporated down. The oil which remained after the evaporation procedure was taken up in 500 ml of methanol, the solution was heated at the boil and then cooled slowly, and the resulting crystal slurry was filtered off. Methanol was added to the heated slurry until the cyrstals went into solution. The material which crystallized out on cooling the methanolic solution was filtered off, recrystallized once again from methanol and dried to give 58 g of a mixtue of the diastereomeric bisesters of melting point 122° C. and $[\alpha]_D^{20} = -63.8$ (c=2, acetone). The yield was 35% of theory, based on the chromanyl ester used in this stage, and the optical purity was 100%.

(c) 58 g (119 millimoles) of the pure ester mixture obtained as described in Example (1b) were heated at the boil with 500 ml of methanol and 132 ml of 1N potassium hydroxide solution for 2 hours. Working up this hydrolysis mixture in a conventional manner by extraction with methylene chloride gave the desired (S)-2,5,7,8-tetramethyl-6-hydroxy-2-(2-hydroxyethyl)-chroman in a total yield of 26% of theory, based on the racemic hydroxyethyl chroman used. Mp.=155° C.; $[\alpha]_D^{20} = -6.95°$ (c=2, ethanol).

EXAMPLE 2

Preparation of (R)-2,5,7,8-tetramethyl-6-hydroxy-2-(2-hydroxyethyl)-chroman

This compound was prepared by a method similar to that described in Example 1, using D-(4-chloro-2-methylphenoxy)-propionyl chloride as the reagent for effecting resolution. The yield was 29% of theory, based on the racemic hydroxyethyl chroman used. Mp.=155° C.; $[\alpha]_D^{20} = +7.00°$ (c=2, acetone).

EXAMPLE 3

Preparation of (S)-2,5,7,8-tetramethyl-6-hydroxy-2-(2-hydroxyethyl)-chroman by embodiment (b) with esterification of the phenolic hydroxyl group 10 g (40 millimoles) of racemic 2,5,7,8-tetramethyl-6-hydroxy-2-(2-hydroxyethyl)-chroman were esterified in the presence of 200 ml of toluene and 0.1 g of p-toluenesulfonic acid by heating for 4 hours with 8.6 g (40 millimoles) of (−)-naphth-1-yloxypropionic acid, water being separated off. The reaction mixture obtained was cooled and then extracted by shaking with sodium bicarbonate solution and water, and the organic phase was evaporated down. The resulting crude ester was then dissolved in 40 ml of pyridine, 4 g of acetic anhydride were added to the solution, and the mixture was left to stand for 24 hours at room temperature. The crude bisester mixture (158 g) obtained by working up in a conventional manner was subjected twice to fractional crystallization from ethanol. The yield of the S form was 29% of theory, based on the racemate, ie. 58% of the theoretically possible amount. Mp.=145° C.; $[\alpha]_D^{20} = -39.0°$ (c=2, chloroform).

Alkaline hydrolysis of the bisester by a method similar to that described in Example 1c gave the desired (S)-2,5,7,8-tetramethyl-6-hydroxy-2-(2-hydroxyethyl)-chroman in 26% yield, based on the racemic compound used. $[\alpha]_D^{20} = -7.0$ (c=2, ethanol); mp.=155° C.

EXAMPLE 4

Preparation of (R)-2,5,7,8-tetramethyl-6-hydroxy-2-(2-hydroxyethyl)-chroman

The compound was prepared by a method similar to that described in Example 3, using (+)-naphth-1-yloxypropionic acid as the reagent for effecting resolution.

EXAMPLE 5

Preparation of (R)-2,5,7,8-tetramethyl-6-hydroxy-2-(2-hydroxyethyl)-chroman by embodiment (b), without esterification of the phenolic hydroxyl group.

10 g (40 millimoles) of racemic 2,5,7,8-tetramethyl-6-hydroxy-2-(2-hydroxyethyl)-chroman were esterified in the presence of 200 ml of toluene and 0.1 g of p-toluenesulfonic acid by heating for 4 hours with 8.6 g (40 millimoles) of (−)-naphth-1-yloxypropionic acid, water being separated off. The crude ester (16 g) obtained by working up in a conventional manner was then dissolved in 90 ml of methanol. This solution was seeded with 20 mg of (R)-2,5,7,8-tetramethyl-6-hydroxychroman-2-ylethyl (−)-naphth-1-yloxypropionate, after which a precipitate formed in the course of two days at −20° C. This precipitate was separated off and was once again recrystallized in the same manner.

The yield was 26%, based on the racemic chroman used. Mp. = 121° C.; $[\alpha]_D^{25} = -41°$ (c=2, CHCl$_3$).

4 g of the ester prepared in this manner were dissolved in 140 ml of methanol, and the solution was refluxed with 9.0 ml of 1M KOH for 1.5 hours. Working up by a procedure similar to that described in Example 1c gave 2.1 g of (R)-2,5,7,8-tetramethyl-6-hydroxy-2-(2-hydroxyethyl)-chroman.

Mp. = 155° C.; $[\alpha]_D^{20} = +6.95$ (c=2, ethanol).

EXAMPLE 6

Preparation of (S)-2,5,7,8-tetramethyl-6-hydroxy-2-(2-hydroxyethyl)-chroman

This compound was prepared by a procedure similar to that described in Example 5, using (+)-naphth-1-yloxypropionic acid as the reagent for effecting resolution.

EXAMPLE 7

Preparation of (S)-2,5,7,8-tetramethyl-6-hydroxy-2-(2-hydroxyethyl)-chroman

The combined mother liquors from Example 5 were evaporated down, 3 g of acetic anhydride and 30 ml of pyridine were added, and the mixture was left to stand for 24 hours. Working up the reaction mixture by hydrolysis with ice water, extraction with methylene chloride, washing and evaporating down the organic phase, and recrystallization of the resulting precipitate twice from ethanol gave 6.6 g of (S)-2,5,7,8-tetramethyl-6-acetoxychroman-2-ylethyl (−)-naphth-1-yloxypropionate of melting point 145° C. and $[\alpha]_D^{20} = -38.7$ (c=2, chloroform). The yield was 34%, based on chromanol used in Example 5.

4 g of the ester prepared in this manner were dissolved in 140 ml of methanol, and the solution was refluxed with 16.4 ml of 1M KOH for 1.5 hours. Working up by a procedure similar to that described in Example 1c gave the desired (S)-chromanyl ethanol in a yield of 31% of theory, based on racemic chromanol used.

EXAMPLE 8

5.5 g of triphenylphosphine were dissolved in 100 ml of anhydrous methylene chloride, 3.4 g of bromine were added dropwise, the reaction mixture was stirred for 30 minutes at room temperature, 5 g of (S)-2,5,7,8-tetramethyl-6-hydroxy-2-(2-hydroxyethyl)-chroman were added, and the mixture was refluxed for one hour and then poured onto sodium carbonate solution. The aqueous phase was extracted with methylene chloride, the combined organic phases were washed with sodium chloride solution, dried and evaporated down, and the residue was recrystallized from methanol. 5.3 g of (S)-2,5,7,8-tetramethyl-6-hydroxy-2-(2-bromoethyl)-chroman were obtained. $[\alpha]_D^{20} = -15$ (c=2, MeOH), mp. = 120° C.

EXAMPLE 9

(R)-2,5,7,8-tetramethyl-6-hydroxy-2-(2-bromoethyl)-chroman was prepared from (R)-2,5,7,8-tetramethyl-6-hydroxy-2-(2-hydroxyethyl)-chroman by a procedure similar to that described in Example 8. $[\alpha]_D^{20} = +15.1$ (c=2, MeOH), mp. = 120° C.

EXAMPLE 10

A mixture of 2 g of (S)-2,5,7,8-tetramethyl-6-hydroxy-2-(2-hydroxyethyl)-chroman, 8 g of carbon tetrachloride and 2.6 g of triphenylphosphine was refluxed for 3 hours, after which the reaction mixture was allowed to cool, the precipitate formed was filtered off under suction and the filtrate was chromatographed over silica gel, using a 5:1 hexane/acetone solvent mixture. 1.7 g of (S)-2,5,7,8-tetramethyl-6-hydroxy-2-(2-chloroethyl)-chroman were obtained. $[\alpha]_D^{20} = -9.1°$ (c=2, chloroform), mp. = 111° C.

EXAMPLE 11

(R)-2,5,7,8-tetramethyl-6-hydroxy-2-(2-chloroethyl)-chroman was prepared from (R)-2,5,7,8-tetramethyl-6-hydroxy-2-(2-hydroxyethyl)-chroman by a procedure similar to that described in Example 10. $[\alpha]_D^{20} = +9.0$, (c=2, chloroform), mp. = 111° C.

EXAMPLE 12

5 g of (S)-2,5,7,8-tetramethyl-6-hydroxy-2-(2-hydroxyethyl)-chroman were suspended in 250 ml of methylene chloride, and isobutene was passed through the suspension. After 15 minutes, 1 ml of concentrated sulfuric acid was added, and stirring was then continued for a further 4 hours at room temperature, while a gentle stream of isobutene was passed through. The mixture was then left to stand overnight in a closed vessel. The organic phase was washed with sodium bicarbonate solution and with water, and was then dried and evaporated down. The crude product was purified over silica gel, using a 5:1 hexane/acetone solvent mixture. 4.5 g of (S)-2,5,7,8-tetramethyl-6-hydroxy-2-(2-tert.-butoxyethyl)-chroman were obtained as a colorless oil. $[\alpha]_{365}^{20} = +4.23°$ (c=2, ethanol).

EXAMPLE 13

(R)-2,5,7,8-tetramethyl-6-hydroxy-2-(2-tert.-butoxyethyl)-chroman was obtained from (R)-2,5,7,8-tetramethyl-6-hydroxy-2-(2-hydroxyethyl)-chroman by a procedure similar to that described in Example 12. $[\alpha]_D^{20} = 4.2$ (c=2, ethanol).

EXAMPLE 14

(S)-2,5,7,8-Tetramethyl-6-hydroxy-2-(2-acetoxyethyl)-chroman was obtained from (S)-2,5,7,8-tetramethyl-6-hydroxy-2-(2-hydroxyethyl)-chroman by a proce-

We claim:

1. A process for the preparation of optically active chroman derivatives of formula (Ia) or (Ib)

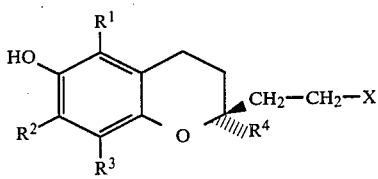

(Ia)

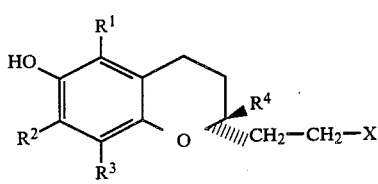

(Ib)

wherein $R^1$, $R^2$, $R^3$ and $R^4$ are each independently a hydrogen atom or a $C_{1-4}$ alkyl group, and X is OH, said process comprising:

(i) selectively converting a racemate of the formula (I')

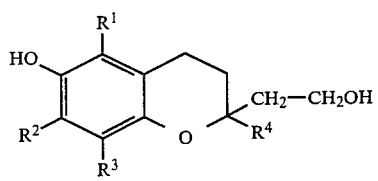

(I')

with a carboxylic acid of formula (II)

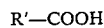R'—COOH (II)

wherein R' is a $C_{1-4}$—alkyl group, or selectively converting a racemate of formula (I') with a lower alkyl ester of the said carboxylic acid of formula (II), to obtain an ester of formula (I'')

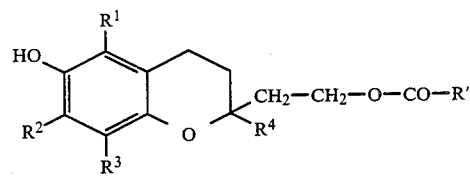

(I'')

(ii) acylating the said ester of formula (I'') with an optically active carboxylic acid halide of formula (III)

$R^5$—CH(OAr)—CO—Y (III)

wherein $R^5$ is a $C_1$-$C_3$ alkyl group, Y is a chlorine atom or a bromine atom, and Ar is a phenyl group, a 1-naphthyl group or a 2-naphthyl group which are unsubstituted or substituted by no more than two substituents selected from the group consisting of $C_{1-4}$—alkyl groups, $C_{1-4}$—alkoxy groups, a chlorine atom, a bromine atom, a cyano group and an nitro group, or acylating the said ester of formula (I'') with a carboxylic anhydride of formula (V)

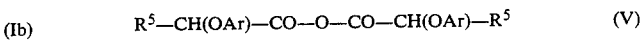

$R^5$—CH(OAr)—CO—O—CO—CH(OAr)—$R^5$ (V)

to obtain a chroman derivative of formula (IV),

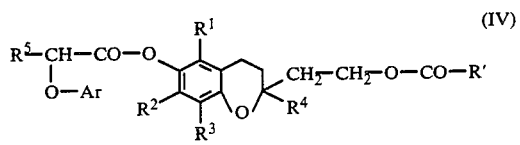

(IV)

which consists of two diastereomeric esters;

(iii) resolving the two said diastereomeric esters by fractional crystallization to obtain pure diastereomers; and (iv) hydrolyzing the said pure diastereomers to obtain the alcohols of formula (Ia) or (Ib).

2. The process of claim 1, further comprising converting the said group X of the said alcohols of formula (Ia) or (Ib) into a group —O—CO—$R^6$, —O$R^6$, —O—tosyl, —O—mesyl, —O—benzenesulfonyl, Cl, Br or I, where $R^6$ is a $C_{1-4}$ alkyl group.

3. The process of claim 1, further comprising converting the said group X of the said alcohol of formula (Ia) or (Ib) into a —O—CO—$R^6$ group, wherein $R^6$ is a $C_{1-4}$ alkyl group.

4. The process of claim 1, further comprising converting the said group X of one of the said alcohols of formula (Ia) or (Ib) into a —O—C(CH$_3$)$_3$ group, by reacting a solution of one of the said alcohols of formula (Ia) or (Ib) in CH$_2$CL$_2$ with isobutene in the presence of sulfuric acid.

5. The process of claim 1, further comprising converting the said group X of one of the said alcohols of formula (Ia) or (Ib) into a chlorine atom, by reacting one of the said alcohols of formula (Ia) or (Ib) with CCl$_4$ and triphenylphosphine.

6. The process of claim 1, further comprising converting the said group X of one of the said alcohols of formula (Ia) or (Ib) into a bromine atom, by reacting one of the said alcohols of formula (Ia) or (Ib) with Br$_2$ and triphenylphosphine in anhydrous CH$_2$Cl$_2$.

* * * * *